United States Patent

Mizutani et al.

[11] Patent Number: 5,578,024
[45] Date of Patent: Nov. 26, 1996

[54] DISPOSABLE BODY FLUIDS ABSORBENT PADDING

[75] Inventors: Satoshi Mizutani, Kawanoe; Hideaki Kitaoka, Funabashi, both of Japan

[73] Assignee: Uni-Charm Corporation, Ehime-ken, Japan

[21] Appl. No.: 461,906

[22] Filed: Jun. 5, 1995

[30] Foreign Application Priority Data

Jul. 6, 1994 [JP] Japan .................. 6-124975

[51] Int. Cl.$^6$ .................. A61F 13/15; A61F 13/20
[52] U.S. Cl. .................. 604/380; 604/370; 604/378; 604/385.1
[58] Field of Search .................. 428/131, 137, 428/138, 139; 604/358, 365–367, 370, 378–380, 381–384, 385.1

[56] References Cited

U.S. PATENT DOCUMENTS 4,079,739  3/1978  Whitehead ................ 604/380
4,634,440  1/1987  Widlund et al. ............ 604/385.1
4,781,962  11/1988  Zamarripa et al. ......... 428/138
5,383,870  1/1995  Takai et al. ............... 604/358

FOREIGN PATENT DOCUMENTS 57-1340  1/1982  Japan.

Primary Examiner—John G. Weiss
Assistant Examiner—P. Zuttarelli
Attorney, Agent, or Firm—Lowe, Price, LeBlanc & Becker

[57]  ABSTRACT

A disposable body fluids absorbent padding at least comprising a liquid-permeable topsheet, a liquid-impermeable backsheet and a liquid-absorbent core disposed between these two sheets, wherein said topsheet is made of a nonwoven fabric comprising high density zones and low density zones, and said high density zones have strips of liquid-impermeable thermoplastic film bonded to the upper surfaces of said high density zones.

16 Claims, 2 Drawing Sheets

000
DISPOSABLE BODY FLUIDS ABSORBENT PADDING

BACKGROUND OF THE INVENTION

The present invention relates to a disposable body fluids absorbent padding and more particularly, to a disposable body fluids absorbent padding such as a menstruation pad, a diaper for infants, a diaper for incontinence and the like having a topsheet capable of concealing body fluids having been absorbed by a core in the padding.

It is well known to use a hydrophobic nonwoven fabric as material for a topsheet not only to alleviate an uncomfortable feeling of wetness for a wearer's skin due to body fluids but also to enhance a body fluids permeability. However, this topsheet is generally poor in its capability of preventing body fluids once having been absorbed by the core, from flowing backward (i.e., resulting in rewetting) and often gives a wearer the feeling of wetness due to such backward flow. This topsheet is also poor in concealing the body fluids having been absorbed by the core and, for example, in the case of a menstruation pad, the core smeared with menstrual discharge is often uncomfortably remarkable for a wearer when the used pad is disposed.

In connection with the above-mentioned smear concealing capability of the topsheet, Japanese Laid-Open Patent Application No. Sho 57 - 1340 teaches that it is effective to use a hydrophobic film having openings each of an equivalent hydraulic diameter less than 0.025 inches as the topsheet. This reference teaches also that a thin layer comprising uniformly distributed fluff pulp or synthetic fiber may be bonded to the inner surface of the film with the thin layer being in contact with the core during use and thereby body fluids permeation to the core may be promoted. However, the film disclosed in this reference is nothing but so-called plastic film presenting the touch falling far short of that presented by a nonwoven fabric and too closely contacting a wearer's skin, often causing stuffiness or eruption.

In view of these problems, it is a principal object of the invention to provide an improved disposable body fluids absorbent padding allowing the above-mentioned problems left behind by the prior art unsolved to be solved by using a topsheet made of a nonwoven fabric comprising high density zones and low density zones, each of said high density zones being provided on its upper surface with a strip of plastic film bonded thereto.

SUMMARY OF THE INVENTION

The object set forth above is achieved, according to the invention, by a disposable body fluids absorbent padding at least comprising a liquid-permeable topsheet, a liquid-impermeable backsheet and a liquid-absorbent core disposed between these two sheets, wherein said topsheet comprises a liquid-permeable nonwoven fabric and a liquid-impermeable thermoplastic film integrally bonded to the upper surface of said nonwoven fabric so as to partially expose the upper surface of said nonwoven fabric, and wherein each zone of said nonwoven fabric covered with said plastic film is of a high density while each zone of said nonwoven fabric not covered with said plastic film is of a low density.

Preferably, each of said high density zones presents a density corresponding to 1.4 times or higher than a density presented by each of said low density zones and said high density zones and said low density zones are alternately arranged so as to form a striped pattern.

Preferably, component fibers of said nonwoven fabric in said high density zones are arranged substantially with a desired orientation.

Preferably, said plastic film is substantially translucent or opaque.

In the body fluids absorbent padding constructed as described above, the topsheet is exposed to a wearer's skin in the low density zones but the high density zones are covered with the respective strips of plastic film. Most of discharged body fluids is absorbed through the low density zones into the liquid-absorbent core, then diffuses in a direction of thickness as well as in a direction of the surface of said core. As a result, the core becomes so-called smeared. The core smeared with body fluids is partially covered with the strips of plastic film partially covering the topsheet and therefore the smear is not remarkable. A quantity of body fluids staying in the low density zones is transferred under the capillary action into the high density zones which are also smeared with body fluids but the strips of plastic film covering these high density zones effectively conceal such smear. On the other hand, a quantity of body fluids staying in the low density zones is effectively reduced owing to said transfer and therefore the smear in these low density zones is also not remarkable.

PREFERRED EMBODIMENTS OF THE INVENTION

Details of a disposable body fluids absorbent padding will be more readily understood from the following description of a typical embodiment in the form of a menstruation pad made in reference with the accompanying drawings.

Figure 1:
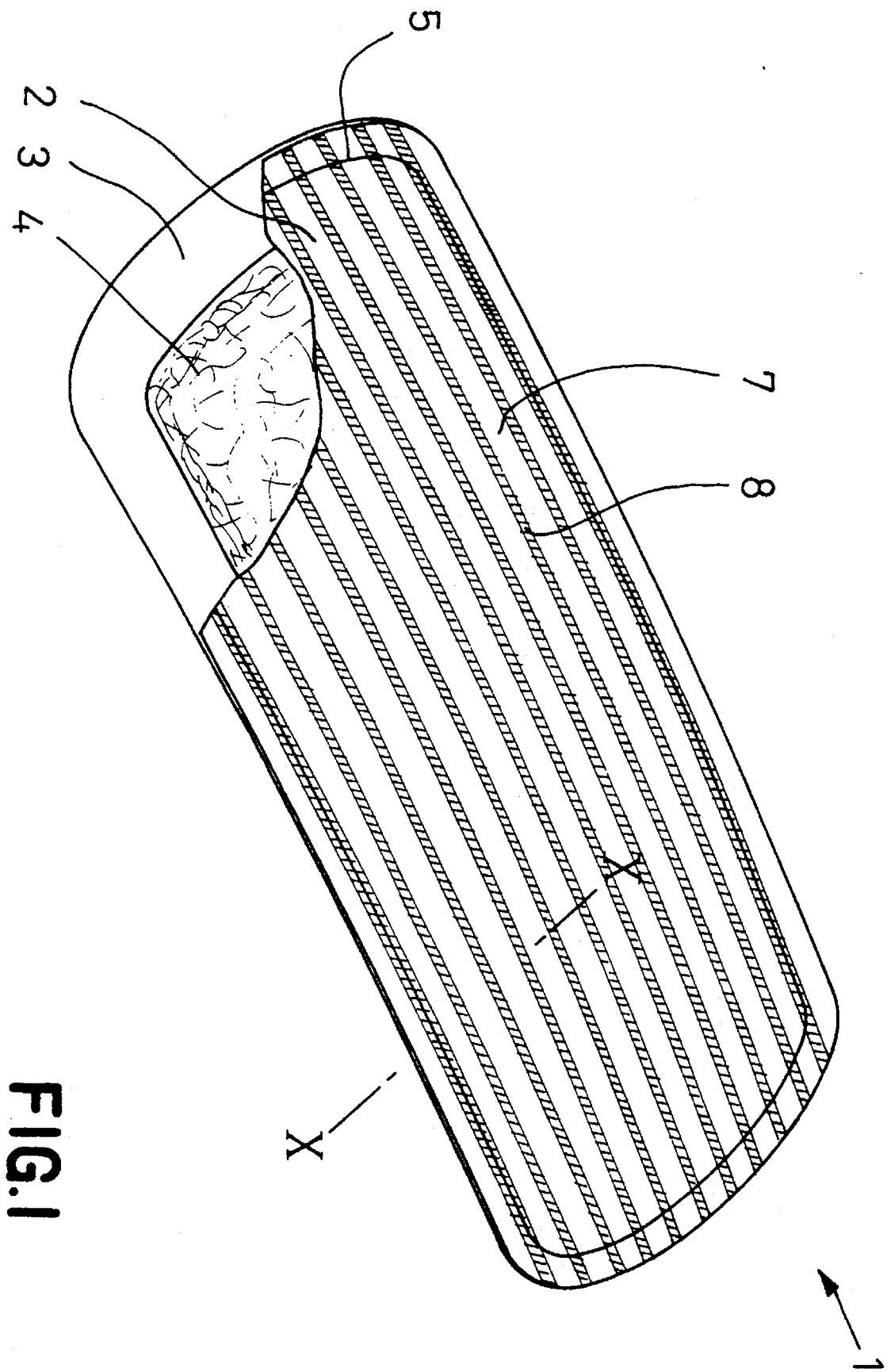
FIG. 1 is a perspective view showing a menstruation pad according to the invention as partially broken away.

Referring to FIG. 1, a pad 1 comprises a topsheet 2, a backsheet 3 and a liquid-absorbent core 4 disposed between these two sheets 2, 3 wherein the top- and backsheets 2, 3 are water-tightly bonded to each other by a sealing line 5 along their portions extending outward beyond a peripheral edge of the core 4. The topsheet 2 is made of a liquid-permeable nonwoven fabric 7 provided on its upper surface with a plurality of longitudinal strips 8 of substantially translucent or opaque plastic films which are liquid-impermeable or air-permeable but liquid-impermeable and preferably water-repellent. The backsheet 3 is made of a liquid-impermeable plastic film. The liquid-absorbent core 4 is made of fluff pulps mixed with high water absorption polymer powders and this mixture may be further mixed with thermoplastic synthetic fibers or entirely covered with a tissue paper.

Figure 2:
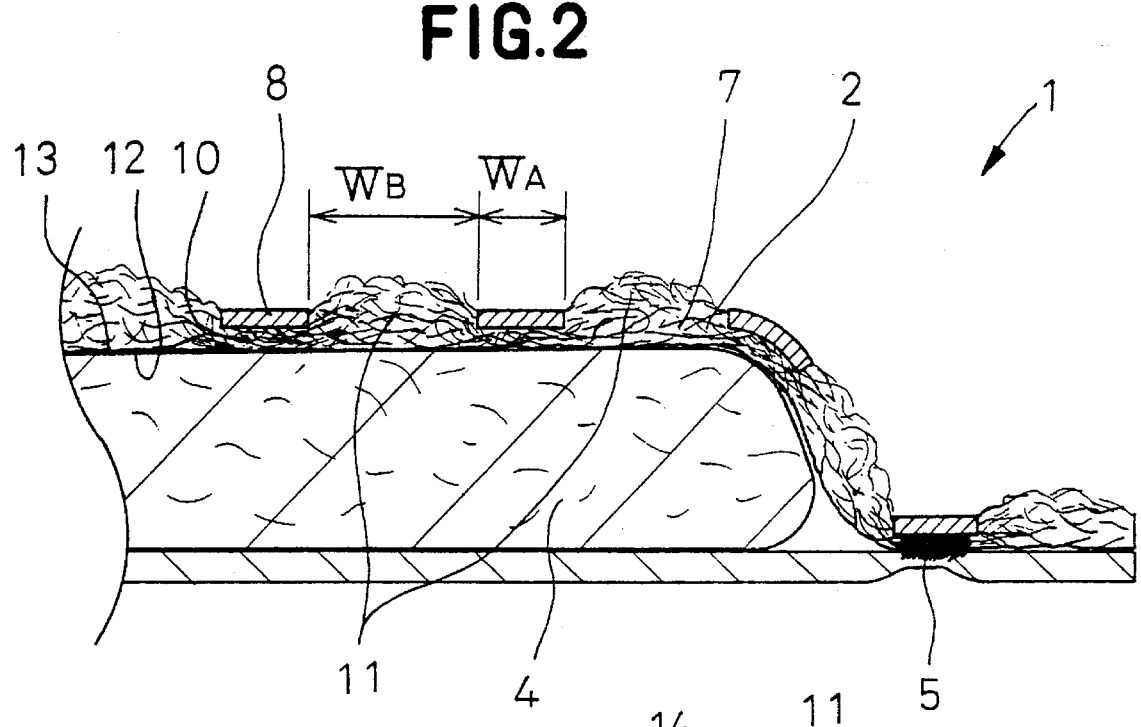
FIG. 2 is a sectional view taken along a line X—X in FIG. 1.

Referring to FIG. 2, the nonwoven fabric 7 forming the topsheet 2 comprises transversely alternate longitudinal high and low density zones 10, 11 of width $W_A$, $W_B$, respectively, which alternate transversely of the pad 1. Each of the high density zones 10 has its upper surface covered with the film strip 8 of the width $W_A$ bonded thereto and each of the low density zones 11 has its upper surface exposed to a wearer's skin. The nonwoven fabric 7 preferably comprises 20 to 100% by weight of thermoplastic synthetic fibers so as to present a weight per unit area of 5 to 200 g/m$^2$ wherein the high density zone 10 has a density of 0.03 or higher and the low density zone 11 has a density of 0.005 to 0.4, i.e., the density of the zone 10 is 1.4 times or higher than the density of the zone 11. These densities should be understood here to be apparent densities calculated on the basis of thicknesses which were measure under a surface pressure of 3 g/cm$^2$ exerted on the nonwoven fabric. While the pad 1 is shown as having the high density zones 10 and the film strip 8 heat sealed together under a pressure, this sealing may be achieved also with use of suitable adhesive or by disposing other weldable film strips between the high density zones 10 and the film strips 8.

The topsheet 2 has its lower surface 12 in contact with the upper surface 13 of the core 4 so that menstrual discharge may be guided through the topsheet 2 into the core 4. More specifically, menstrual discharge can permeate only the low density zones 11, then is guided into the underlying core 4 having a high water holding capacity as well as into the adjacent high density zones 10, and substantially no quantity of menstrual discharge stays in the low density zones 11. The core 4 as well as the high density zones 10 thus smeared with menstrual discharge are partially or entirely covered with the film strips 8 effectively serving to prevent this smear from being remarkable. The topsheet 2 functioning in this manner will facilitate menstrual discharge to be guided longitudinally of the pad 1 in the density zones 10 and allow the respective high density zones 10 to be effectively utilized from end to end when fibers at least in the high density zones 10 are oriented longitudinally of the pad 1. Additionally, the top surfaces of the low density zones 11 are higher than those of the film strips 8 and form mountain- or wave-like shapes (See FIG. 2). It is obvious that the pad 1 gives a wearer no feeling of wetness due to the absorbed quantity of menstrual discharge.

Figure 3:
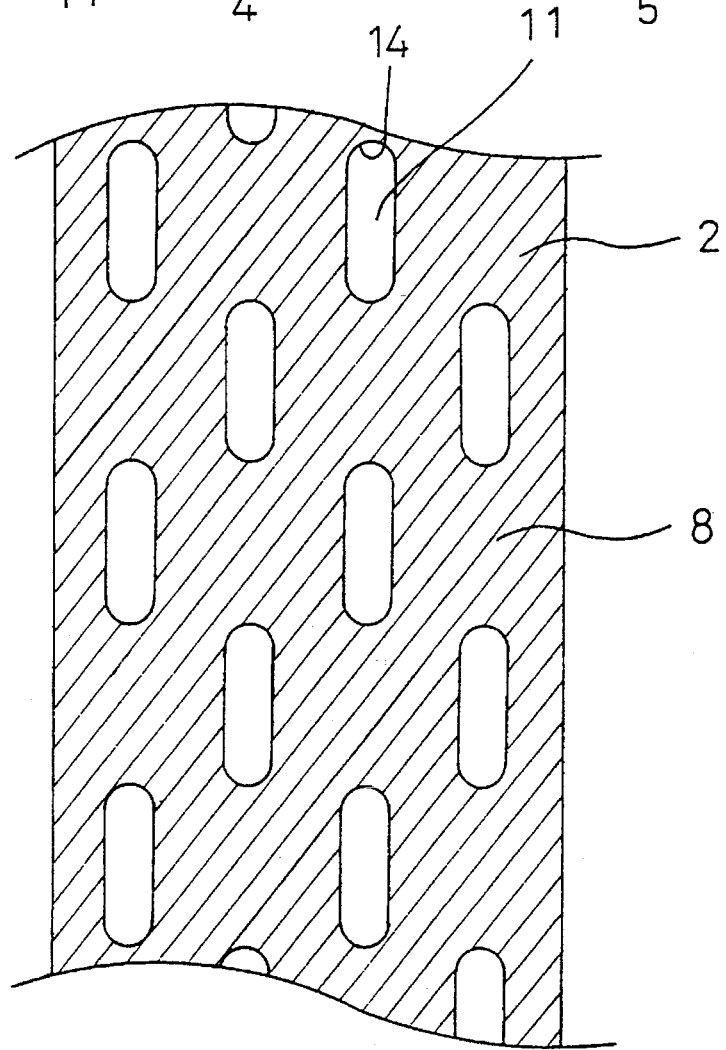
FIG. 3 is a plan view showing a variant of a topsheet used in the embodiment shown in FIG. 1.

Referring to FIG. 3, elliptical low density zones 11 are intermittently arranged in a plastic film 8 which is continuous both in length and width and the high density zone 10 (not shown) bonded to the film 8 that is, the film 8 extends both in length and width and has a plurality of longitudinally long elliptical apertures 14 where the low density zones 11 substantially in the same form as said apertures 14 are positioned, so that menstrual discharge once having been transferred to the high density zone 10 may be further diffused both longitudinally and transversely as viewed in FIG. 3 and thereby the high density zone 10 may be utilized more efficiently than in the case shown by FIG. 1.

While an area ratio between the high density zones 10 and the low density zones 11 in the topsheet 2 is not critical to the invention, it is preferred for menstruation pads or disposable diapers to be designed so that the high density zones 10 occupy 30 to 70% of the entire topsheet 2. To alleviate an uncomfortable feeling of wetness given by the topsheet 2 impregnated with menstrual discharge, it is preferred to employ a hydrophobic nonwoven fabric. Alternatively and/or additionally, a degree of the hydrophobic nature may be appropriately adjusted by a suitable surface treating agent in order to promote permeation as well as diffusion of menstrual discharge or thermoplastic synthetic fibers may be mixed with 3 to 20% by weight of hydrophilic fibers such as fluff pulps. The previous description "the plastic film is substantially translucent or opaque" should be understood to mean that such plastic film will effectively prevent the core as well as the high density zones smeared with menstrual discharge from being seen therethrough. The preferable film includes a colored film and transparent film having an aventurine coated surface.

As will be apparent from the foregoing description, the nonwoven fabric forming the topsheet comprises the high density zones and the low density zones arranged alternately and the high density zones are provided on their upper surfaces with the plastic film bonded thereto so that, even after body fluids have been transferred from the low density zones to the high density zones and the core, the plastic film effectively prevent the high density zones and the core smeared with body fluids being remarkably seen therethrough. In addition, a quantity of body fluids which may stay in the low density zones is relative small and therefore a wearer can dispose the used padding without uncomfortable feeling. A substantially translucent or opaque plastic film may be used as said film to enhance the desired concealing effect.

In the respective high density zones, the component fibers of the nonwoven fabric may be arranged with a desired orientation to effectively and entirely utilize each of the high density zone.

What is claimed is:

1. A disposable body fluids absorbent padding comprising a liquid-permeable topsheet, a liquid-impermeable backsheet and a liquid-absorbent core disposed between said topsheet and backsheet, wherein said topsheet comprises a liquid-permeable nonwoven fabric and liquid-impermeable thermoplastic film integrally bonded to the upper surface of said nonwoven fabric so as to partially expose the upper surface of said nonwoven fabric, and wherein each zone of said nonwoven fabric covered with said plastic film is of high density while each zone of said nonwoven fabric not covered with said plastic film is of low density;

wherein the top surface of said low density zones are higher than that of said film.

2. A disposable body fluids absorbent padding comprising a liquid-permeable topsheet, a liquid-impermeable backsheet and a liquid-absorbent core disposed between said topsheet and backsheet, wherein said topsheet comprises a liquid-permeable nonwoven fabric and liquid-impermeable thermoplastic film integrally bonded to the upper surface of said nonwoven fabric so as to partially expose the upper surface of said nonwoven fabric, and wherein each zone of said nonwoven fabric covered with said plastic film is of a high density while each zone of said nonwoven fabric not covered with said plastic film and extending generally co-elevationally adjacent the high density zone is of low density.

3. The padding according to claim 2, wherein said high density zones and said low density zones are alternately arranged transversely of said padding so as to form a striped pattern extending longitudinally of said padding.

4. The padding according to claim 2, wherein said high density zones are intermittently arranged transversely and longitudinally of said padding.

5. The padding according to claim 2, wherein each of said high density zones presents a density corresponding to 1.4 times or higher than a density presented by each of said low density zones.

6. The padding according to claim 2, wherein component fibers of said nonwoven fabric in said high density zones are arranged substantially with a desired orientation.

7. The padding according to claim 2, wherein said plastic film is substantially translucent or opaque.

8. A disposable body fluid absorbent padding comprising:

a liquid-permeable topsheet;

a liquid-impermeable backsheet;

a liquid-absorbent core disposed between said topsheet and said backsheet;

said topsheet comprising a liquid-permeable nonwoven fabric containing thermoplastic synthetic fibers and a liquid-impermeable thermoplastic film integrally welded to the upper surface of said nonwoven fabric so as to partially expose the upper surface of said nonwoven fabric;

each zone of said nonwoven fabric covered with said plastic film having a high density while each zone of said nonwoven fabric not covered with said plastic film having a low density; and each of said high density zones and said low density zones extending longer in the longitudinal direction of said padding than in the transverse direction of said padding.

9. The padding according to claim 8, wherein said high density zones and said low density zones are alternately arranged transversely of said padding so as to form a striped pattern extending longitudinally of said padding.

10. The padding according to claim 8, wherein said high density zones are intermittently arranged transversely and longitudinally of said padding.

11. The padding according to claim 8, wherein each of said high density zones presents a density corresponding to 1.4 times or higher than a density presented by each of said low density zones.

12. The padding according to claim 8, wherein component fibers of said nonwoven fabric in said high density zones are arranged substantially with a desired orientation.

13. The padding according to claim 8, wherein said plastic film is substantially translucent or opaque.

14. A disposable body fluids absorbent padding comprising:

a liquid-permeable topsheet;

a liquid-impermeable backsheet;

a liquid-absorbent core disposed between said topsheet and said backsheet;

said topsheet comprising a liquid-permeable nonwoven fabric containing thermoplastic synthetic fibers and a liquid-impermeable thermoplastic film integrally welded to the upper surface of said nonwoven fabric so as to partially expose the upper surface of said nonwoven fabric;

each zone of said nonwoven fabric covered with said plastic film having a high density while each zone of said nonwoven fabric not covered with said plastic film having a low density; and the top surface of said low density zones being higher than that of said film.

15. The padding according to claim 14, wherein said high density zone has a density of at least 0.03 and said low density zone has a density of at least 0.005.

16. The padding according to claim 14, wherein said high density zones occupy 30 to 70% of the entire said topsheet.

* * * * *